(12) United States Patent
Kawasaki et al.

(10) Patent No.: US 12,102,727 B2
(45) Date of Patent: Oct. 1, 2024

(54) CONTINUOUS DECONTAMINATION AND STERILIZATION DEVICE

(71) Applicant: AIREX CO., LTD., Nagoya (JP)

(72) Inventors: Koji Kawasaki, Nagoya (JP); Daisuke Kakuda, Nagoya (JP); Yoshitaka Ogata, Nagoya (JP); Jun Masudome, Nagoya (JP); Haruka Futamura, Nagoya (JP); Tsukasa Kitano, Nagoya (JP); Zhiqiang Guo, Nagoya (JP)

(73) Assignee: AIREX CO., LTD. (JP)

( * ) Notice: Subject to any disclaimer, the term of this patent is extended or adjusted under 35 U.S.C. 154(b) by 0 days.

(21) Appl. No.: 18/557,149

(22) PCT Filed: Jan. 18, 2023

(86) PCT No.: PCT/JP2023/001303
§ 371 (c)(1),
(2) Date: Oct. 25, 2023

(87) PCT Pub. No.: WO2023/157540
PCT Pub. Date: Aug. 24, 2023

(65) Prior Publication Data
US 2024/0261452 A1    Aug. 8, 2024

(30) Foreign Application Priority Data
Feb. 16, 2022   (JP) .................. 2022-021805

(51) Int. Cl.
*B65B 55/02* (2006.01)
*A61L 2/08* (2006.01)
(Continued)

(52) U.S. Cl.
CPC ............... *A61L 2/26* (2013.01); *A61L 2/087* (2013.01); *A61L 2/22* (2013.01); *B65B 51/20* (2013.01);
(Continued)

(58) Field of Classification Search
CPC ....... B65B 55/027; B65B 55/24; B65B 55/08; B65B 55/04; A61L 2/08; A61L 2/18; A61L 2/20; A61L 2/26
See application file for complete search history.

(56) References Cited

U.S. PATENT DOCUMENTS 3,783,581 A * 1/1974 Pierce .................... B65B 55/10
53/167
3,799,220 A * 3/1974 Berry ....................... B67C 3/04
141/46
(Continued)

FOREIGN PATENT DOCUMENTS

JP    H10218128 A    8/1998
JP    2004236806 A    8/2004
(Continued)

OTHER PUBLICATIONS

Sekiguchi, M., Electron Beam Irradiation System, Radiation Utilization Technology Database, 2007, 9 pages.
(Continued)

*Primary Examiner* — Andrew M Tecco
(74) *Attorney, Agent, or Firm* — Quarles & Brady LLP; Yakov S. Sidorin

(57) ABSTRACT

A continuous decontamination-and-sterilization device possessing high efficiency, reliability, and safety of operation to treat external surfaces of a package that is conveyed to a sterile working chamber. A decontamination chamber decontaminates (with a decontamination agent) bottom and lateral external surfaces of the package conveyed by a first conveyance, with an upper surface seal portion of the package being sealed. An aeration chamber removes residue of decontamination agent from an external surface of the package while the package is conveyed by a second conveyance means. A sterilization chamber sterilizes the upper surface seal portion of the package by irradiating electron
(Continued)

beams as the package is conveyed by a third conveyance means, with the bottom or lateral external surface of the package being supported. The first conveyance means includes a sealing means by an adsorbing function to adsorb and capture the upper surface seal portion so as to seal the same and convey the package, with the bottom and lateral external surface portions of the package being open.

6 Claims, 6 Drawing Sheets

(51) Int. Cl.
| | |
|---|---|
| *A61L 2/22* | (2006.01) |
| *A61L 2/26* | (2006.01) |
| *B65B 51/20* | (2006.01) |
| *B65B 55/08* | (2006.01) |
| *B65B 55/24* | (2006.01) |
| *B65D 65/38* | (2006.01) |
| *B65D 77/20* | (2006.01) |

(52) U.S. Cl.
CPC ............ *B65B 55/027* (2013.01); *B65B 55/08* (2013.01); *B65B 55/24* (2013.01); *B65D 65/38* (2013.01); *B65D 77/2024* (2013.01); *A61L 2202/11* (2013.01); *A61L 2202/122* (2013.01); *A61L 2202/123* (2013.01); *A61L 2202/13* (2013.01); *A61L 2202/15* (2013.01); *A61L 2202/182* (2013.01); *A61L 2202/23* (2013.01); *B65D 2565/388* (2013.01)

(56) References Cited

U.S. PATENT DOCUMENTS

| | | | | |
|---|---|---|---|---|
| 3,911,640 | A | * | 10/1975 | Rausing .................... A61L 2/10 53/167 |
| 4,424,659 | A | * | 1/1984 | Perigo ................ B65D 77/2024 53/436 |
| 5,025,611 | A | * | 6/1991 | Garwood ........... B65D 81/2076 53/511 |
| 6,039,922 | A | * | 3/2000 | Swank .................. B65B 61/186 53/425 |
| 2013/0092196 | A1 | * | 4/2013 | Nagatani .................. B08B 9/32 134/94.1 |
| 2015/0108366 | A1 | * | 4/2015 | Kawasaki ................. A61L 2/08 250/453.11 |
| 2018/0344884 | A1 | * | 12/2018 | Kawasaki ............... B65B 55/08 |
| 2022/0193290 | A1 | * | 6/2022 | Kawasaki ........... B05B 17/0607 |

FOREIGN PATENT DOCUMENTS

| | | |
|---|---|---|
| JP | 2007076714 A | 3/2007 |
| JP | 4237489 B2 | 3/2009 |
| JP | 2012029859 A | 2/2012 |
| JP | 5603700 B2 | 10/2014 |
| JP | 2016220747 A | 12/2016 |
| JP | 2020168181 A | 10/2020 |

OTHER PUBLICATIONS

PCT International Search Report and Written Opinion, PCT/JP2023/001303, Mar. 7, 2023, 9 pages [English Language Translation of ISR Only].

* cited by examiner

CONTINUOUS DECONTAMINATION AND STERILIZATION DEVICE

CROSS-REFERENCE TO RELATED APPLICATIONS

This application is a US national phase of pending International Application No. PCT/JP2023/001303 filed on Jan. 18, 2023 and now published as WO 2023/157540, which designates the United States and claims priority from Japanese Patent Applications No. 2022-021805 filed on Feb. 16, 2022. The disclosure of each of these patent applications is incorporated herein by reference.

TECHNICAL FIELD

The present invention relates to a continuous decontamination and sterilization device for decontaminating and sterilizing external surfaces of a package accommodating a sterilized article and conveying the decontaminated and sterilized package to a working chamber in a sterile environment.

RELATED ART

The convenience in the clinical environment allows for proactive use of pre-filled syringes and vials filled beforehand with a pharmaceutical product and recent increased production thereof. Each pharmaceutical product is filled in these syringes or vials in a filling working chamber in a sterile environment (a sterile working chamber such as an isolator). Each of the syringes and vials used in this operation is small in size, and such tools to be treated are needed in large numbers. Then, these syringes and vials are sterilized by y-ray irradiation, electron beam irradiation, EOG (ethylene oxide gas), and other approaches at each manufacturing stage, and carried in a sterile working chamber with a predetermined number thereof integrally accommodated in a package.

Illustrative example of the package includes a medical appliance package proposed in the following patent document 1 and disclosed as prior art. Such a package is generally referred to as "peel-open package", and includes a plastic tab molded according to the shape of an article such as a syringe or vial accommodated therein and a gas-permeable upper surface seal. The upper surface seal used is generally Tyvek (trademark) as a non-woven fabric composed of high-density polyethylene microfibers, and the Tyvek (trademark) is gas-permeable through micropores included in the Tyvek (trademark) product to the inside of the plastic tab, but blocks ingress of microorganisms.

The package thus configured is further packed on the exterior with a packaging bag to be circulated and conveyed. Unfortunately, when the package is circulated or conveyed, or taken out of the packaging bag to carry the same in a sterile working chamber, external surfaces of the plastic tab and the upper surface seal are contaminated. Therefore, such a contaminated package is not allowed to be carried in the sterile working chamber unless the external surfaces are decontaminated or sterilized. Then, after the external surfaces of the plastic tab and the upper surface seal are decontaminated or sterilized by a decontamination device or a sterilization device connected to the sterile working chamber, the package is conveyed to the sterile working chamber, the upper surface seal is peeled open from the plastic tab in the sterile working chamber, and the filling into an internal sterilized syringe or vial is performed.

Various methods using EOG (ethylene oxide gas), hydrogen peroxide low-temperature gas, ozone gas, plasma, y-ray irradiation, ultraviolet irradiation or electron beam irradiation are introduced for each intended use in the decontamination device and the sterilization device. One of these methods is the most common decontamination method using hydrogen peroxide low-temperature gas.

The method using a hydrogen peroxide low-temperature gas can acquire a required level of decontamination effect, but unfortunately requires some processing time to decontaminate the entire package and another processing time to remove the hydrogen peroxide condensed therein when the hydrogen peroxide low-temperature gas enters the inside of a plastic tab through an upper surface seal composed of Tyvek (trademark).

Thus, in a decontamination device or a sterilization device where numerous articles are required to be treated per unit time, as in the production of pre-filled syringes, short-time treatment methods with high decontamination and sterilization effects are preferable. The following Non-Patent Document 1 describes a safe sterilization device integrated with a small electron beam irradiator (small electron accelerator) for acquiring a high sterilization effect as opposed to general devices using a hydrogen peroxide low-temperature gas and others, and for providing high productivity and no residual material.

In fact, the sterilization device is operated to treat a package which accommodates pre-filled syringes, and the package including prior-sterilized syringes is conveyed to a sterile working chamber by a conveyor after external surfaces of the package are sterilized with electron beams. The device, composed of 3 small electron accelerators arranged at an angle of 120 degrees with each other, irradiates all the surfaces of the package in 3 directions.

In the device, the 3 small electron accelerators, arranged at an angle of 120 degrees with each other, are simultaneously operated to sterilize the entire external surfaces of a medical appliance package for sterilization. The small electron accelerator is expensive per unit and has a service limit (life), depending on the total service time. Therefore, the initial and maintenance costs of the device are unfortunately higher due to simultaneous operation of the 3 devices.

In addition, each time the 3 small electron accelerators come to the end of their respective irregular service limits (life), the efficiency of sterilization not only significantly declines due to each required considerable time for replacement, but the reliability and safety of sterilization effects are also impeded. Simultaneous replacement of the 3 accelerators in a predetermined period of time may overcome this problem, but this approach causes another problem of higher maintenance costs.

Then, to solve the aforementioned problem, inventors of the present invention proposed a continuous decontamination and sterilization device and a method for decontamination and sterilization previously disclosed in the following Patent Document 2. The continuous decontamination and sterilization device decontaminates and sterilizes external surfaces of a package and sterilizes with one small electron accelerator only an upper surface seal portion of the package with possible ingress of a decontamination gas as the package is conveyed to a sterile working chamber. On the other hand, the device efficiently decontaminates with a decontamination gas such as a hydrogen peroxide gas bottom and lateral external surface portions of a package allowing for no ingress of the decontamination gas.

CITATION LIST

Patent Literature

Patent Document 1: JP-A-4237489
Patent Document 2: JP-A-5603700

Non-Patent Literature

Non-Patent Document 1: Radiation Application Technology Database, Data Number: 010306 (Prepared by Masayuki Sekiguchi on Oct. 3, 2007), Radiation Application Development Association

SUMMARY OF THE INVENTION

Technical Problem

In fact, the continuous decontamination and sterilization device disclosed in the above Patent Document 2 can have reduced initial and maintenance costs by a combined use of one small electron accelerator and a decontamination gas. However, the device is provided with a plurality of special chambers accommodating bottom and lateral external surface portions of a package to prevent ingress of a decontamination gas from an upper surface seal to the inside of the package. Thus, the device needs a complex mechanism for allowing these chambers to circulate inside a decontamination chamber.

Thus, the present invention was made in view of the situation to solve the problems, and has an object to provide a continuous decontamination and sterilization device having high decontamination and sterilization effects and high productivity and capable of maintaining high levels of reliability and safety of the decontamination and sterilization effects in a simple structure when external surfaces of a package are decontaminated and sterilized as the package is conveyed to a sterile working chamber.

Solution to the Problem

To solve the aforementioned problem, inventors of the present invention have carried out an extended investigation to find that a combined use of one small electron accelerator and a decontamination agent leads to a method for readily and reliably sealing an upper surface seal and a method for using a decontamination agent can be devised. Based on that technique, the present invention was accomplished.

Specifically, a continuous decontamination and sterilization device according to one implementation of the idea of the present invention includes,
 a continuous decontamination and sterilization device (100 to 400) connected to a sterile working chamber (170 to 470) for decontaminating and sterilizing an external surface portion of an accommodate-package (P) with an upper surface seal portion (P2) having gas permeability and conveying the accommodate-package to the inside of the sterile working chamber, including
 a decontamination chamber (120 to 420) for decontaminating with a decontamination agent bottom and lateral external surface portions of the accommodate-package as the accommodate-package is conveyed by a first conveyance means (30, 60, 70, 80), with the upper surface seal portion of the accommodate-package sealed,
 an aeration chamber (130 to 430) for removing the decontamination agent which is residual at the external surface portion of the accommodate-package after decontamination as the accommodate-package is conveyed by a second conveyance means (30, 15, 70, 80), and
 a sterilization chamber (150 to 450) for sterilizing the upper surface seal portion of the accommodate-package by irradiating electron beams from an electron accelerator (50) as the accommodate-package is conveyed with the bottom or lateral external surface portion of the accommodate-package supported by a third conveyance means (13), characterized in that
 the first conveyance means includes a sealing means by an adsorbing function, the sealing means including a plurality of suction ports which opens to a plurality of adsorption surfaces which conforms to the shape of the upper surface seal portion of the accommodate-package, the suction ports suctioning the accommodate-package to adsorb and capture the upper surface seal portion of the accommodate-package so as to seal the same and convey the accommodate-package, with the bottom and lateral external surface portions of the accommodate-package open.

Moreover, a continuous decontamination and sterilization device according to the implementation of the idea of the present invention includes, in one embodiment,
 a continuous decontamination and sterilization device connected to a sterile working chamber for decontaminating and sterilizing an external surface portion of an accommodate-package with an upper surface seal having gas permeability and conveying the accommodate-package to the inside of the sterile working chamber, including
 a decontamination chamber for decontaminating with a decontamination agent bottom and lateral external surface portions of the accommodate-package as the accommodate-package is conveyed by a first conveyance means, with the upper surface seal portion of the accommodate-package sealed,
 an aeration chamber for removing the decontamination agent which is residual at the external surface portion of the accommodate-package after decontamination as the accommodate-package is conveyed by a second conveyance means, and
 a sterilization chamber for sterilizing the upper surface seal portion of the accommodate-package by irradiating electron beams from an electron accelerator as the accommodate-package is conveyed by a third conveyance means, with the bottom or lateral external surface portion of the accommodate-package supported, characterized in that
 the first conveyance means includes a sealing means by a pressing function, the sealing means including a sealing member (70a, 80a) located at an upper portion of the decontamination chamber for sealing the upper surface seal portion of the accommodate-package and a pressing member (70b, 80b) located at a lower portion of the decontamination chamber for pressing the accommodate-package from a bottom surface thereof, and the accommodate-package is conveyed, with the accommodate-package vertically sandwiched between the sealing member and the pressing member.

Furthermore, at least one embodiment of the present invention is characterized in that
 the decontamination chamber includes a mist supply means (41) for supplying to the inside of the decontamination chamber a mist for decontamination converted from the decontamination agent and a mist dispersion means (42) including an ultrasonic vibrating board generating sound flows by ultrasound from board surfaces, characterized in that the mist for decontamination supplied to the inside of the decontamination chamber is pressed by acoustic radiation pressure to decontaminate the bottom and lateral external surface portions of the accommodate-package conveyed by the first conveyance means.

Moreover, at least one embodiment of the present invention is characterized in that the accommodate-package carried from the external environment is transferred from the first conveyance means in the decontamination chamber to the second conveyance means in the aeration chamber and transferred from the second conveyance means to the third conveyance means in the sterilization chamber to be sterilized after decontamination and aeration.

Moreover, at least one embodiment of the present invention is characterized in that the accommodate-package carried from the external environment is transferred from the first conveyance means in the decontamination chamber to the third conveyance means in the sterilization chamber and transferred from the third conveyance means to the second conveyance means in the aeration chamber to be aerated after decontamination and sterilization.

Furthermore, at least one embodiment of the present invention is characterized in that the first conveyance means in the decontamination chamber and the second conveyance means in the aeration chamber are an integral fourth conveyance means (30, 70, 80) operated with each other, characterized in that the bottom and lateral external surface portions of the accommodate-package are decontaminated and aerated as the accommodate-package is conveyed by the fourth conveyance means inside the decontamination chamber and the aeration chamber, with the upper surface seal portion of the accommodate-package sealed.

Furthermore, at least one embodiment of the present invention is characterized in that the fourth conveyance means in the decontamination chamber includes a sealing means by an adsorbing function, characterized in that the sealing means includes a plurality of suction ports which opens to a plurality of adsorption surfaces which conforms to the shape of the upper surface seal portion of the accommodate-package to adsorb and capture the upper surface seal portion of the accommodate-package so as to seal the same and convey the accommodate-package, with the bottom and lateral external surface portions of the accommodate-package open.

Furthermore, at least one embodiment of the present invention includes, is characterized in that the fourth conveyance means in the decontamination chamber includes a sealing means by a pressing function, characterized in that the sealing means includes a sealing member (70*a*, 80*a*) located at an upper portion of the decontamination chamber for sealing the upper surface seal portion of the accommodate-package and a pressing member (70*b*, 80*b*) located at a lower portion of the decontamination chamber for pressing the accommodate-package from a bottom surface thereof, characterized in that the accommodate-package is conveyed, with the accommodate-package vertically sandwiched between the sealing member and the pressing member.

Furthermore, at least one embodiment of the present invention is characterized in that the pressing member presses upward at least one portion of the bottom surface of the accommodate-package by point contact.

Furthermore, at least one embodiment of the present invention is characterized in that the pressing member presses upward the bottom surface of the accommodate-package by spring repulsion.

Furthermore, at least one embodiment of the present invention is characterized in that the sealing member seals the upper surface seal portion of the accommodate-package by supporting a decontamination agent decomposition catalyst.

The reference letters in parenthesis of each of the above means correspond to the specific means described in each of the following embodiments.

Advantageous Effects Produced by an Embodiment of the Invention

According to the above configuration, a continuous decontamination and sterilization device according to the present invention includes a decontamination chamber, an aeration chamber and a sterilization chamber, which are connected to a sterile working chamber. In the decontamination chamber, bottom and lateral external surface portions of an accommodate-package are decontaminated with a decontamination agent as the accommodate-package is conveyed by a first conveyance, with an upper surface seal portion of the accommodate-package sealed. In the aeration chamber, the decontamination agent which is residual at the external surface portion of the accommodate-package after decontamination is removed as the accommodate-package is conveyed by a second conveyance means. In the sterilization chamber, the upper surface seal portion of the accommodate-package is sterilized by irradiating electron beams from an electron accelerator as the accommodate-package is conveyed by a third conveyance means, with the bottom or lateral external surface portion of the accommodate-package supported.

Accordingly, in the decontamination chamber, the bottom and lateral external surface portions of the accommodate-package allowing for no ingress of decontamination agent are efficiently decontaminated with a decontamination agent, with the upper surface seal portion of the accommodate-package with possible ingress of a decontamination agent sealed. Meanwhile, in the sterilization chamber, only the upper surface seal portion of the accommodate-package with possible ingress of a decontamination agent is sterilized by one small electron accelerator. Accordingly, a continuous decontamination and sterilization device, having high decontamination and sterilization effects and high productivity and capable of maintaining high levels of reliability and safety of the decontamination and sterilization effects in a simple structure, can be provided.

According to the above configuration, the decontamination chamber may include a mist supply means and a mist dispersion means. The mist supply means converts a decontamination agent into a mist for decontamination, and supplies the same to the inside of the decontamination chamber. Also, the mist dispersion means includes an ultrasonic vibrating board generating sound flows by ultrasound from board surfaces to decontaminate the bottom and lateral external surface portions of the accommodate-package by pressing with acoustic radiation pressure the mist for decontamination supplied to the inside of the decontamination chamber. Accordingly, the decontamination effect is rendered efficient and the above operational advantage can more specifically be provided.

According to the above configuration, the accommodate-package carried from the external environment is directly or indirectly transferred from the first conveyance means in the decontamination chamber to the second conveyance means in the aeration chamber. Next, the accommodate-package is directly or indirectly transferred from the second conveyance means to the third conveyance means in the sterilization chamber. Therefore, the accommodate-package is decontaminated and sterilized after aeration. Meanwhile, according to another configuration, the accommodate-package carried from the external environment is directly or indirectly transferred from the first conveyance means in the decontamination chamber to the third conveyance means in the sterilization chamber. Next, the accommodate-package is directly or indirectly transferred from the third conveyance means to the second conveyance means in the aeration chamber. Therefore, the accommodate-package is decontaminated and aerated after sterilization. Accordingly, the decontamination agent which is residual at an external surface portion of the accommodate-package after decontamination may be removed just after decontamination or after decontamination and then sterilization.

According to the above configuration, the first conveyance means in the decontamination chamber and the second conveyance means in the aeration chamber may be an integral fourth conveyance means operated with each other. In this case, the bottom and lateral external surface portions of the accommodate-package can be decontaminated and aerated as the accommodate-package is conveyed by the fourth conveyance means inside the decontamination chamber and the aeration chamber arranged in parallel, with the upper surface seal portion of the accommodate-package sealed. Accordingly, the above operational advantage can more specifically be provided.

According to the above configuration, the first conveyance means in the decontamination chamber and the fourth conveyance means in the decontamination chamber and the aeration chamber may include a sealing means by an adsorbing function. The sealing means can adsorb and capture the upper surface seal portion of the accommodate-package so as to seal the same and convey the accommodate-package, with the bottom and lateral external surface portions of the accommodate-package open. In fact, the sealing means preferably includes a plurality of adsorption surfaces which conforms to the shape of the upper surface seal portion of the accommodate-package. Therefore, the upper surface seal portion of the accommodate-package is effectively sealed and the bottom and lateral external surface portions of the accommodate-package are effectively decontaminated. Accordingly, the above operational advantage can more specifically be provided.

According to the above configuration, the first conveyance means in the decontamination chamber and the fourth conveyance means in the decontamination chamber and the aeration chamber may include a sealing means by a pressing function. Herein, the sealing means comprises a sealing member located at an upper portion of the decontamination chamber for sealing the upper surface seal portion of the accommodate-package and a pressing member located at a lower portion of the decontamination chamber for pressing the accommodate-package from a bottom surface thereof. Therefore, the accommodate-package is conveyed, with the accommodate-package vertically sandwiched between the sealing member and the pressing member.

According to the above configuration, the pressing member may press upward at least one portion of the bottom surface of the accommodate-package by point contact. Meanwhile, according to another configuration, the pressing member may press upward the bottom surface of the accommodate-package by spring repulsion. Therefore, the accommodate-package can be conveyed, with the accommodate-package vertically sandwiched between the sealing member and the pressing member. At this time, the sealing means may seal the upper surface seal portion of the accommodate-package by supporting a decontamination agent decomposition catalyst. Accordingly, the above operational advantage can more specifically be provided.

DESCRIPTION OF EMBODIMENTS

In sterile working chambers for manufacturing pharmaceutical products, advanced decontamination validation is required in accordance with Good Manufacturing Practice (GMP). In addition, materials for pre-filled syringes or vials used in a sterile working chamber are essentially sterilized with a sterilization level of 6 Log Spore Reduction (LRD) or more according to GMP standards.

To meet this requirement, in the present invention, the "decontamination" level is guaranteed such that the Sterility Assurance Level (SaL) is $10^{-6}$ or less, or SaL$\leq 10^{-1}$. The method for guaranteeing this level of decontamination may be to use hydrogen peroxide in the form of a gas or mist.

Meanwhile, in the present invention, the "sterilization" level is guaranteed such that the Sterility Assurance Level is $10^{-12}$ or less, or SaL$\leq 10^{-2}$. The method for guaranteeing this level of sterilization may be to use electron beam irradiation with a required radiation dose of 25 kGv (see the ISO-13409 standard).

Figure 1:
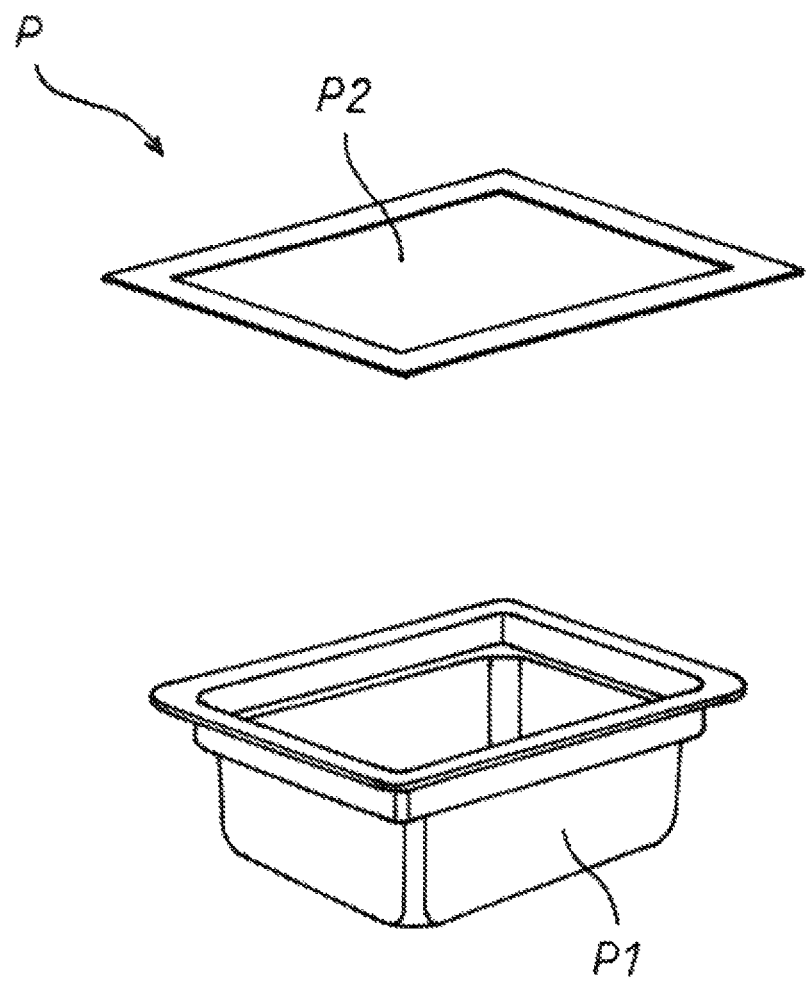
FIG. 1 is a perspective view illustrating an accommodate-package to be decontaminated and sterilized (medical appliance package) according to each embodiment.

Each embodiment of a continuous decontamination and sterilization device according to the present invention will be described with reference to the drawings. In a continuous decontamination and sterilization device according to each of the following embodiments, an accommodate-package to be decontaminated and sterilized will be explained. FIG. 1 is a perspective view illustrating an accommodate-package to be decontaminated and sterilized (medical appliance package) according to each embodiment. In FIG. 1, a package P includes a polyethylene tab P1 and an upper surface seal portion P2 of Tyvek (trademark). The tab P1 and the upper surface seal portion P2 are tightly sealed with a heat seal. In each embodiment, numerous sterilized syringes used for filling a pre-filled syringe inside the package P are accommodated and external surfaces are decontaminated and sterilized with the package P tightly sealed.

First Embodiment

Figure 2:
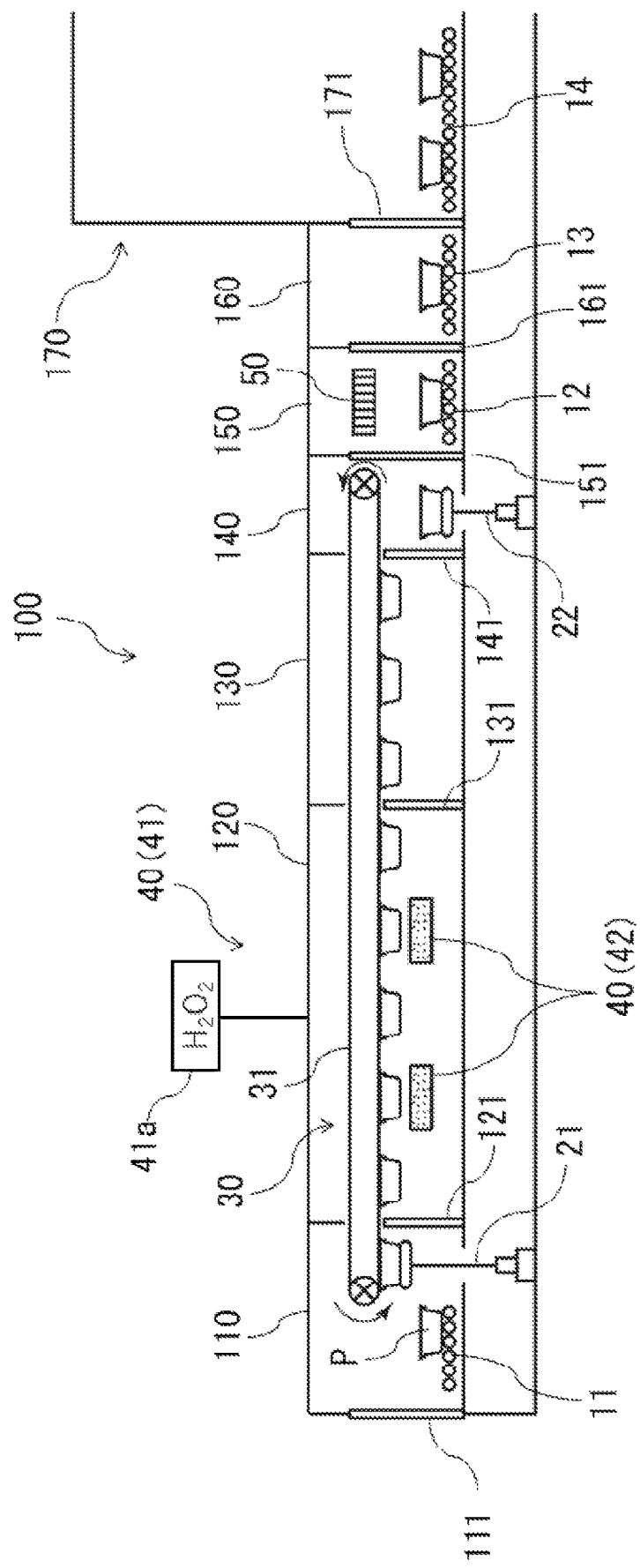
FIG. 2 is a schematic cross-sectional view illustrating a continuous decontamination and sterilization device according to a first embodiment seen in a lateral direction.

FIG. 2 is a schematic cross-sectional view illustrating a continuous decontamination and sterilization device according to a first embodiment seen in a lateral direction. In FIG. 2, a continuous decontamination and sterilization device 100 is connected to a sterile working chamber (isolator 170) for filling a pre-filled syringe therein. The continuous decontamination and sterilization device 100 is composed of a box body configured by a wall portion formed of a stainless metal plate, the inside of which is divided into a carrying pass box 110, a decontamination chamber 120, an aeration chamber 130, a prior-to-sterilization pass box 140, a sterilization chamber 150, and an after-sterilization pass box 160 by each wall portion.

A front wall portion of the carrying pass box 110 is provided with an openable/closable shutter 111. A common wall portion between the carrying pass box 110 and the decontamination chamber 120 is provided with an openable/closable shutter 121. A common wall portion between the decontamination chamber 120 and the aeration chamber 130 is provided with an openable/closable shutter 131. A common wall portion between the aeration chamber 130 and the prior-to-sterilization pass box 140 is provided with an openable/closable shutter 141. A common wall portion between the prior-to-sterilization pass box 140 and the sterilization chamber 150 is provided with an openable/closable shutter 151. A common wall portion between the sterilization chamber 150 and the after-sterilization pass box 160 is provided with an openable/closable shutter 161. A common wall portion between the after-sterilization pass box 160 and an isolator 170 connected thereto is provided with an openable/closable shutter 171.

Thus, in the continuous decontamination and sterilization device 100 according to the first embodiment, the decontamination chamber 120 for decontaminating bottom and lateral external surface portions (an external surface portion of a tab P1) of a package P is disposed on the front side. Next, the aeration chamber 130 for removing the decontamination agent which is residual at the external surface portion of the decontaminated tab P1 is disposed. Next, the sterilization chamber 150 for sterilizing an upper surface seal portion P2 of the decontaminated and aerated package P is disposed.

Each of the chambers in the continuous decontamination and sterilization device 100 and the isolator 170 are maintained in a sterile state, each blocked from the external environment. Particularly, to prevent ingress of bacteria into the isolator 170 for filling a pre-filled syringe, the internal air pressure in each of the chambers is set to be higher than that in the external environment by the air supplied from an air supply device (not shown). In addition, the air pressure of the isolator 170 is the highest, which is subsequently reduced through each of the other chambers toward the carrying pass box 110 to maintain the sterile environment.

A roller conveyor 11 and a package lift 21 are provided on the floor of the carrying pass box 110. A ceiling portion from a rear portion of the carrying pass box 110 through the decontamination chamber 120, the aeration chamber 130 to the prior-to-sterilization pass box 140 is provided with a conveyance device 30 (vacuum conveyor 30; details are later described) for adsorbing the upper surface seal portion P2 of the package P and conveying the package P in the direction of the sterilization chamber 150. The roller conveyor 11 conveys the package P carried by opening the shutter 111 in the direction of the decontamination chamber 120. The package lift 21 receives the package P from the roller conveyor 11 at the rear portion of the carrying pass box 110 and transfers the same to the vacuum conveyor 30 at the ceiling portion.

The vacuum conveyor 30 adsorbs and captures the upper surface seal portion P2 of the received package P and conveys the package P to the prior-to-sterilization pass box 140 through the inside of the decontamination chamber 120 and the aeration chamber 130, with the bottom and lateral external surface portions of the package P open. During this operation, the bottom and lateral external surface portions of the package P are decontaminated with a decontamination agent in the decontamination chamber 120 to remove the residual decontamination agent in the aeration chamber 130 (details are later described). As the package P is transferred by the vacuum conveyor 30, the shutters 121, 131, 141 for the respective chambers are opened and closed.

A terminal portion of the vacuum conveyor 30 and a package lift 22 are provided in the prior-to-sterilization pass box 140. The package lift 22 receives the package P from the vacuum conveyor 30, opens the shutter 151 and transfers the same to a roller conveyor 12 in the sterilization chamber 150. In the sterilization chamber 150, the upper surface seal portion P2 of the package P is sterilized with electron beams (details are later described). The sterilized package P is transferred from the roller conveyor 12 in the sterilization chamber 150 to the roller conveyor 13 in the after-sterilization pass box 160 by opening the shutter 161. Subsequently, the package P is transferred from the roller conveyor 13 to the roller conveyor 14 in the isolator 170 by opening the shutter 171. Thus, the package P is carried in the isolator 170 as it has been decontaminated and sterilized.

Figure 3:
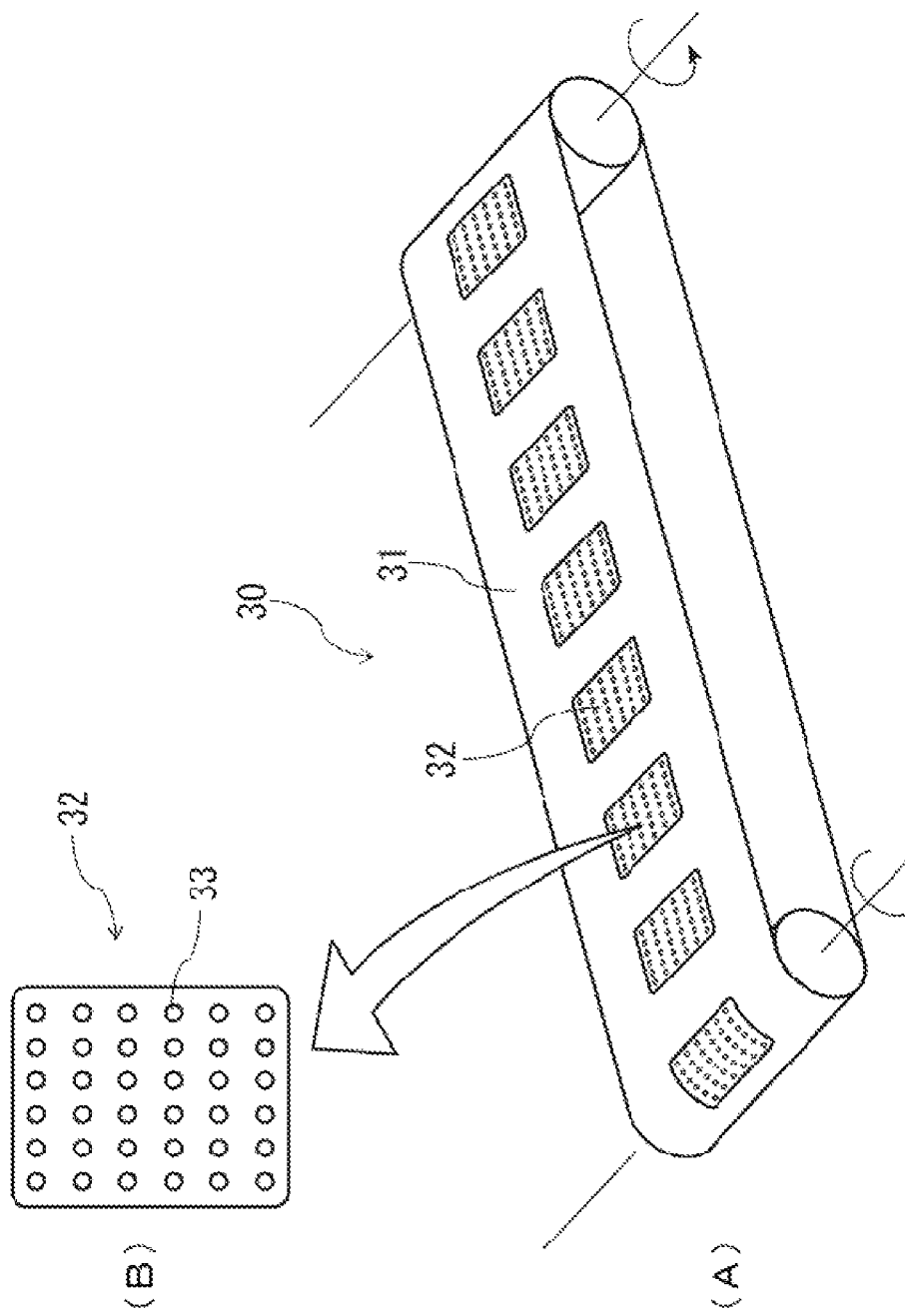
FIG. 3(A) is a perspective view of a belt of a vacuum conveyor of a conveyance device used in the first embodiment of FIG. 2
FIG. 3(B) is an enlarged view of an adsorption surface of the vacuum conveyor of the conveyance device used in the first embodiment of FIG. 2.

Next, the vacuum conveyor 30 will be described. The vacuum conveyor 30 is a belt conveyor-type conveyance device by rotation of a ring-shaped wide belt, which is disposed integrally at the ceiling portion of the chambers from the rear portion of the carrying pass box 110 through the decontamination chamber 120, the aeration chamber 130 to the prior-to-sterilization pass box 140. FIG. 3(A) is a perspective view of a belt of a vacuum conveyor of a conveyance device used in the first embodiment and FIG. 3(B) is an enlarged view of an adsorption surface of the vacuum conveyor of the conveyance device used in the first embodiment. In FIG. 3(A), a belt body 31 of the vacuum conveyor 30 is provided on a surface thereof with a plurality of adsorption surfaces 32. The shape and size of these adsorption surfaces 32 correspond to the shape and size of the upper surface seal portion P2 of the package P.

In addition, in FIG. 3(B), a plurality of suction ports 33 are open on each of the adsorption surfaces 32 of the belt body 31, and the adsorption surface 32 allows a suction pump (not shown) to adsorb and capture the package P at the upper surface seal portion P2. In order to transfer the package P from the package lift 11 in the carrying pass box 110 to the vacuum conveyor 30, a position adjusting mechanism (not shown) is disposed to conform the upper surface seal portion P2 of the package P to the adsorption surface 32.

Next, decontamination operations will be described. The package P captured by the vacuum conveyor 30 is conveyed to the decontamination chamber 120 by opening the shutter 121 of the decontamination chamber 120. The package P is captured with the bottom and lateral external surface portions open, because the upper surface seal portion P2 is adsorbed. Accordingly, the bottom and lateral external surface portions of the package P are decontaminated with the decontamination agent with an advanced level. On the other hand, since the upper surface seal portion P2 is entirely sealed with the adsorption surface 32 of the vacuum conveyor 30, no decontamination agent is allowed to enter the upper surface seal portion P2 to the inside of the package P.

In general, hydrogen peroxide has widely been used (in the form of a gas or mist) as a decontamination agent. Advantageously, hydrogen peroxide has a strong sterilization effect, and is inexpensively available and effectively utilized as an environmentally-friendly decontamination agent which is ultimately resolved into oxygen and water. The decontamination effect by hydrogen peroxide is provided by a condensed film of a hydrogen peroxide solution which condenses on the surface of an article to be decontaminated. Therefore, in the present invention, decontamination may be performed by using either a conventional type of hydrogen peroxide gas or a recently developed hydrogen peroxide mist.

In this first embodiment, an approach of decontamination using a hydrogen peroxide mist is employed and a mist dispersion mechanism using an ultrasonic vibrating board is further employed to enhance the decontamination efficiency. The use of these approaches can streamline a decontamination work (decontamination and aeration operations) by supplying a proper amount of decontamination agent to a package P to make the decontamination effect perfect and shortening the operating time of an aeration operation.

Herein, "mist" is broadly interpreted as the state of a liquid droplet of a decontamination agent refined and floating in the air, the state of a gas and a liquid agent of a decontamination agent in mixture, the state of the decontamination agent to repeat the change in phase between condensation and evaporation of a gas and a droplet, and the like. In terms of particle size as well, the mist is also broadly interpreted to include mists, fogs, and liquid droplets, which can be subclassified. In this first embodiment, ultrasonic vibration of the mist dispersion mechanism converts even a mist, a fog and a liquid droplet sized 3 to 10 μm or more into equalized ultrafine particles 3 μm or less to provide high-level decontamination effects.

In FIG. 2, the decontamination chamber 120 includes a decontamination device 40 therein. The decontamination device 40 is composed of a mist supply unit 41, a mist dispersion unit 42, and a control unit (not shown). In this first embodiment, the mist supply device 41 used is a two-fluid spray nozzle (not shown). The two-fluid spray nozzle converts a hydrogen peroxide solution from an external storage tank 41a into a hydrogen peroxide solution mist by compressed air from a compressor (not shown) to supply the same to the inside of the decontamination chamber 120 from a discharge port (not shown) which opens on a side wall surface of the decontamination chamber 120. In the present invention, the mist supply device is not restricted to a two-fluid spray nozzle, and a mist generation mechanism, an output and the like are not particularly restricted.

The mist dispersion device 42 includes 4 ultrasonic vibrating boards arranged such that two ultrasonic vibrating boards are placed on each of the two side wall surfaces with vibrating surfaces oriented in the internal horizontal direction of the decontamination chamber 120 (only two ultrasonic vibrating boards on an innermost side wall are shown). Each vibrating board includes a base and a plurality of transmitters. In this first embodiment, the base used is a speaker base, and the transmitter used is an ultrasonic speaker. Also, the ultrasonic speakers are arranged so as to be uniform in transmission direction. In this first embodiment, the vibrating board included in the mist dispersion device is not restricted to an ultrasonic speaker, and an ultrasonic generation mechanism, a frequency range, an output and the like are not particularly restricted.

Next, the action of a hydrogen peroxide mist inside the decontamination chamber 120 including the decontamination device 40 according to the above configuration will be described. Ultrasonic vibration of the ultrasonic speaker allows a significantly directional sound flow traveling in the air in the vertical direction (in the left direction shown) from the vibrating surface to take in a hydrogen peroxide mist discharged from the two-fluid spray nozzle to provide pressing force from acoustic radiation pressure. The hydrogen peroxide mist is converted into a fine mist refined by ultrasonic vibration from the sound flow and uniformly dispersed inside the decontamination chamber 120.

Since the fine mist has smaller particle sizes and larger surface areas, it is believed that the evaporation efficiency of mists is high, resulting in repeated evaporation and condensation. The fine mists are highly-refined mists to form a uniform and thin condensed film on bottom and lateral external surface portions of a package P conveyed inside the decontamination chamber 120. Therefore, no condensed film which is thicker and more non-uniform than in a decontamination operation using a conventional hydrogen peroxide gas is generated. Thus, the fine mist of hydrogen peroxide is subjected to constant ultrasonic vibration to repeatedly evaporate and condense on the bottom and lateral external surface portions of the package P for efficient decontamination. Such an efficient decontamination with a small amount of decontamination agent can improve the efficiency of an aeration operation after decontamination.

Next, an aeration operation will be described. The package P captured by the vacuum conveyor 30 is conveyed from the decontamination chamber 120 to the aeration chamber 130 by opening the shutter 131 of the aeration chamber 130. In the aeration chamber 130, the package P is aerated to remove a coagulation membrane of hydrogen peroxide which is residual on the bottom and lateral external surface portions, with the upper surface seal portion P2 captured on the vacuum conveyor 30. The aeration chamber 130 has an air supply device (not shown) for supplying clean air to the inside thereof and an air exhaust device (not shown) for discharging the air containing a hydrogen peroxide gas from inside. The clean air is supplied and discharged similarly as a package is normally aerated. However, in this first embodiment, as described above, such an efficient decontamination with a small amount of decontamination agent can enhance the efficiency of an aeration operation after decontamination.

Next, a sterilization operation will be described. The package P captured by the vacuum conveyor 30 is conveyed to the prior-to-sterilization pass box 140 by opening the shutter 141 of the prior-to-sterilization pass box 140. In the prior-to-sterilization pass box 140, the package lift 22 receives the package P from the terminal portion of the vacuum conveyor 30, and transfers the package P to the roller conveyor 12 in the sterilization chamber 150 by opening the shutter 151. In the sterilization chamber 150, the upper surface seal portion P2 of the package P is sterilized with electron beams. The sterilized package P is transferred from the roller conveyor 12 in the sterilization chamber 150 to the roller conveyor 13 in the after-sterilization pass box 160 by opening the shutter 161.

In this first embodiment, a sterilization region is configured in the prior-to-sterilization pass box 140, the sterilization chamber 150, and the after-sterilization pass box 160. Specifically, the sterilization chamber 150 is configured such that the prior-to-sterilization pass box 140 is defined as a front spare chamber and the after-sterilization pass box 160 is defined as a rear spare chamber. This is because that electron beams irradiated from an electron accelerator included in the sterilization chamber 150 and resulting secondary X rays are safely shielded to leak no such beams to the adjacent aeration chamber 130 or the isolator 170.

Therefore, the apparatus arrangement is preferably designed such that a passage from the prior-to-sterilization pass box 140 to the sterilization chamber 150, a passage of the roller conveyor 12 in the sterilization chamber 150 and a passage of the roller conveyor 13 in the after-sterilization pass box 160 are curved. Moreover, a wall portion and the front and rear shutters 151, 161 of the sterilization chamber 150 are preferably provided as a wall surface structure having favorable X-ray shielding properties. Each of the prior-to-sterilization pass box 140, the sterilization chamber 150 and the after-sterilization pass box 160 is preferably configured to generate unidirectional clean air flowing from below to above. This is because that contaminants at the unsterilized upper surface seal portion P2 don't contaminate the bottom and lateral external surface portions after decontamination.

Also, the sterilization chamber 150 includes one sterilizer (electron accelerator 50) and the roller conveyor 12. The electron accelerator 50 is disposed to orient an irradiation surface downward from an upper portion of the sterilization chamber 150. The roller conveyor 12 is located below relative to the irradiation surface of the electron accelerator 50 to convey the package P at a constant speed. During the conveyance, the upper surface seal portion P2 of the package P is sterilized with electron beams irradiated from the electron accelerator 50. The electron accelerator 50 used may generally be small or low-energy type, e.g., having a radiation source: 40 to 200 kV, 3.5 to 5 mA.

Next, the sterilized package P is transferred from the roller conveyor 12 in the sterilization chamber 150 to the roller conveyor 13 in the after-sterilization pass box 160 by opening the shutter 161. Subsequently, the package P is transferred from the roller conveyor 13 to the roller conveyor 14 in the isolator 170 by opening the shutter 171. Accordingly, the package P is carried to the isolator 170 as it has been decontaminated and sterilized.

As described above, in the continuous decontamination and sterilization device 100 according to this first embodiment, the bottom and lateral external surface portions, or the external surface portion of the tab P1 is first decontaminated with hydrogen peroxide mists, with the upper surface seal portion P2 of the package P sealed in the decontamination chamber 120. Subsequently, the P1 is aerated in the aeration chamber 130 in the similar state. Therefore, the treatment of only the external surface portion of the tab P1 allows for no ingress of hydrogen peroxide gas to the inside of the package P through the upper surface seal portion P2 formed of Tyvek (trademark) having micropores.

In the following sterilization chamber 150, the external surface portion of the upper surface seal portion P2 of the package P is sterilized by electron beams irradiation. An assured high level of sterilization is performed by electron beam radiation on the upper surface seal portion P2, because this portion is formed of Tyvek (trademark) having micropores and directly affects the sterile guarantee after filling in the chemical filling step. In the sterilization chamber 150, since only the external surface portion of the upper surface seal portion P2 of the package P may be irradiated with electron beams, one operating electron accelerator may be provided, initial costs for equipment are low, and replacement operations are easier to reduce maintenance costs. An additional advantage is that the one electron accelerator can be used up to the service limit (life), thereby reduces maintenance costs and further maintains high levels of reliability and safety of the decontamination effect.

Thus, successfully provided in this first embodiment is a continuous decontamination and sterilization device having high decontamination and sterilization effects and high productivity and capable of maintaining high levels of reliability and safety of the decontamination and sterilization effects in a simple structure when external surfaces of a package are decontaminated and sterilized as the package is conveyed to an isolator.

Second Embodiment

Figure 4:
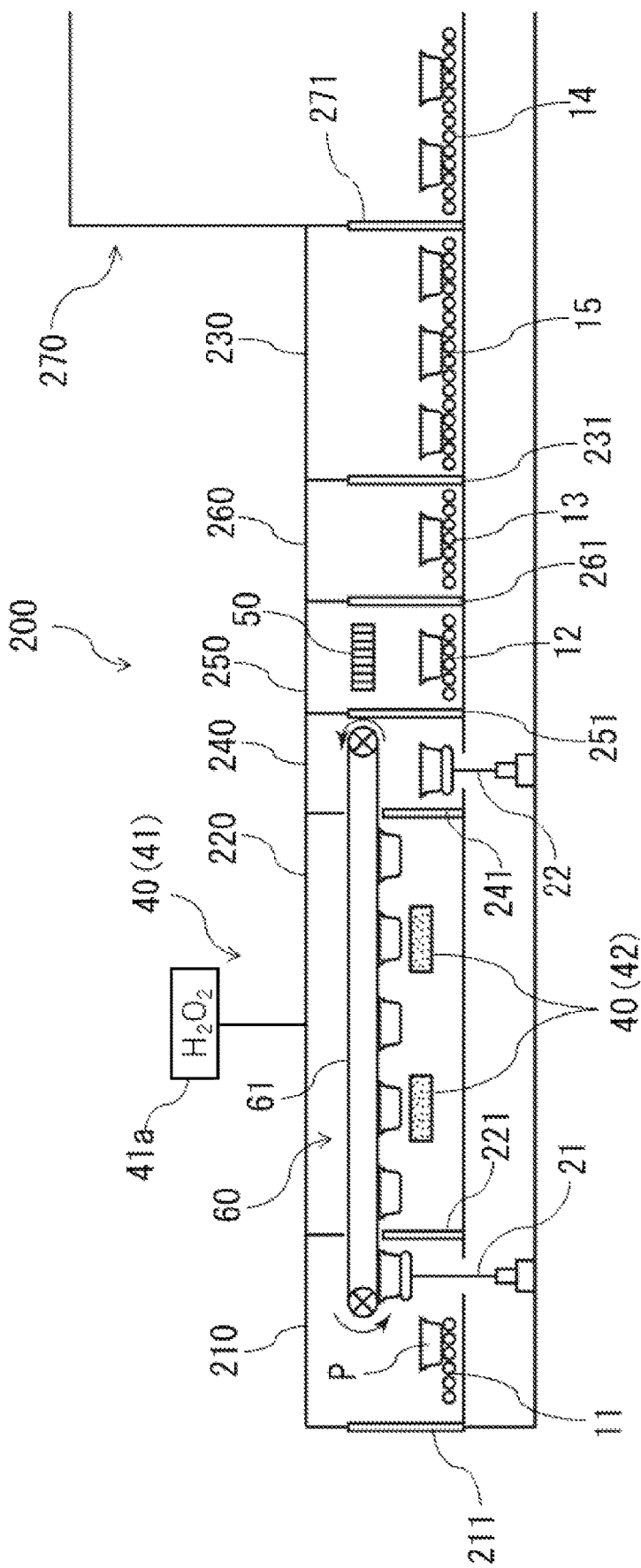
FIG. 4 is a schematic cross-sectional view illustrating a continuous decontamination and sterilization device according to a second embodiment seen in a lateral direction.

FIG. 4 is a schematic cross-sectional view illustrating a continuous decontamination and sterilization device according to a second embodiment seen in a lateral direction. In FIG. 4, a continuous decontamination and sterilization device 200 is connected to a sterile working chamber (isolator 270) for filling a pre-filled syringe therein. The continuous decontamination and sterilization device 200 is composed of a box body configured by a wall portion formed of a stainless metal plate, the inside of which is divided into a carrying pass box 210, a decontamination chamber 220, a prior-to-sterilization pass box 240, a sterilization chamber 250, an aeration chamber 230 and an after-sterilization pass box 260 by each wall portion.

A front wall portion of the carrying pass box 210 is provided with an openable/closable shutter 211. A common wall portion between the carrying pass box 210 and the decontamination chamber 220 is provided with an openable/closable shutter 221. A common wall portion between the decontamination chamber 220 and the prior-to-sterilization pass box 240 is provided with an openable/closable shutter 241. A common wall portion between the prior-to-sterilization pass box 240 and the sterilization chamber 250 is provided with an openable/closable shutter 251. A common wall portion between the sterilization chamber 250 and the after-sterilization pass box 260 is provided with an openable/closable shutter 261. A common wall portion between the after-sterilization pass box 260 and the aeration chamber 230 is provided with an openable/closable shutter 231. A common wall portion between the aeration chamber 230 and an isolator 270 connected thereto is provided with an openable/closable shutter 271.

Thus, in the continuous decontamination and sterilization device 200 according to the second embodiment, the decontamination chamber 220 for decontaminating bottom and lateral external surface portions (an external surface portion of a tab P1) of a package P is disposed on the front side. Next, the sterilization chamber 250 for sterilizing an upper surface seal portion P2 of the decontaminated package P is disposed. Next, the aeration chamber 230 for removing the decontamination agent which is residual at the external surface portion of the decontaminated tab P1 is disposed.

Each of the chambers in the continuous decontamination and sterilization device 200 and the isolator 270 are maintained in a sterile state, each blocked from the external environment. Particularly, to prevent ingress of bacteria into the isolator 270 for filling a pre-filled syringe, the internal air pressure in each of the chambers is set to be higher than in the external environment by the air supplied from an air supply device (not shown). In addition, the air pressure of the isolator 270 is the highest, which is subsequently reduced through each of the other chambers toward the carrying pass box 210 to maintain the sterile environment.

A roller conveyor 11 and a package lift 21 are provided on the floor of the carrying pass box 210. Also, a ceiling portion from a rear portion of the carrying pass box 210 through the decontamination chamber 220 to the prior-to-sterilization pass box 240 is provided with a conveyance device 60 (vacuum conveyor 60) for adsorbing the upper surface seal portion P2 of the package P and conveying the package P in the direction of the sterilization chamber 250. The roller conveyor 11 conveys the package P carried by opening the shutter 211 in the direction of the decontamination chamber 220. The package lift 21 receives the package P from the roller conveyor 11 at the rear portion of the carrying pass box 210 and transfers the same to the vacuum conveyor 60 at the ceiling portion.

The vacuum conveyor 60 adsorbs and captures the upper surface seal portion P2 of the received package P and conveys the same to the prior-to-sterilization pass box 240 through the inside of the decontamination chamber 220, with the bottom and lateral external surface portions of the package P open. Meanwhile, the bottom and lateral external surface portions of the package P are decontaminated with the decontamination agent in the decontamination chamber 220. As the package P is transferred by the vacuum conveyor 60, the shutters 221, 241 for the respective chambers are opened and closed.

The prior-to-sterilization pass box 240 is provided with a terminal portion of the vacuum conveyor 60 and a package lift 22. The package lift 22 receives the package P from the vacuum conveyor 60 and transfers the same to the roller conveyor 12 in the sterilization chamber 250 by opening the shutter 251. In the sterilization chamber 250, the upper surface seal portion P2 of the package P is sterilized with electron beams. The sterilized package P is transferred from the roller conveyor 12 in the sterilization chamber 250 to the roller conveyor 13 in the after-sterilization pass box 260 by opening the shutter 261.

Subsequently, the package P is transferred from the roller conveyor 13 to the roller conveyor 15 in the aeration chamber 230 by opening the shutter 231. In the aeration chamber 230, the package P is aerated to remove the decontamination agent which is residual on the bottom and lateral external surface portions as the package P is conveyed by the roller conveyor 15. Subsequently, the package P is transferred from the roller conveyor 15 to the roller conveyor 14 in the isolator 270 by opening the shutter 271. Accordingly, the package P is carried to the isolator 270 as it has been decontaminated and sterilized.

In this second embodiment, each operation of decontamination, aeration and sterilization is basically performed similarly as in the above first embodiment. However, in this second embodiment, the order of the decontamination and sterilization operations is different from that in the above first embodiment. Specifically, in the above first embodiment, a package is first "decontaminated, aerated and then sterilized". On the other hand, in this second embodiment, a package is first "decontaminated, sterilized and then aerated". In this second embodiment, a condensed film of a decontamination agent is residual on an external surface of the tab P1 of the package P during the sterilization operation. In addition, the upper surface seal portion P2 of the package P is not sealed during the aeration operation.

During the sterilization operation, each of the prior-to-sterilization pass box 240, the sterilization chamber 250 and the after-sterilization pass box 260 is preferably configured to generate unidirectional clean air flowing from above to below. This configuration allows for no ingress of hydrogen peroxide gas vaporized from the condensed film which is residual at the external surface portion of the tab P1 to the inside of the package P from the upper surface seal portion P2. On the other hand, since the condensed film of the decontamination agent is residual at the external surface portion of the tab P1, contaminants on the unsterilized upper surface seal portion P2 don't contaminate the bottom or lateral external surface portion after decontamination.

Even during the aeration operation, the aeration chamber 230 is preferably configured to generate unidirectional clean air flowing from above to below. This configuration allows for no ingress of hydrogen peroxide gas vaporized from the condensed film which is residual at the exterior portion of the tab P1 to the inside of the package P from the upper surface seal portion P2.

Thus, successfully provided in this second embodiment is a continuous decontamination and sterilization device having high decontamination and sterilization effects and high productivity and capable of maintaining high levels of reliability and safety of the decontamination and sterilization effects in a simple structure when external surfaces of a package are decontaminated and sterilized as the package is conveyed to an isolator.

Third Embodiment

Figure 5:
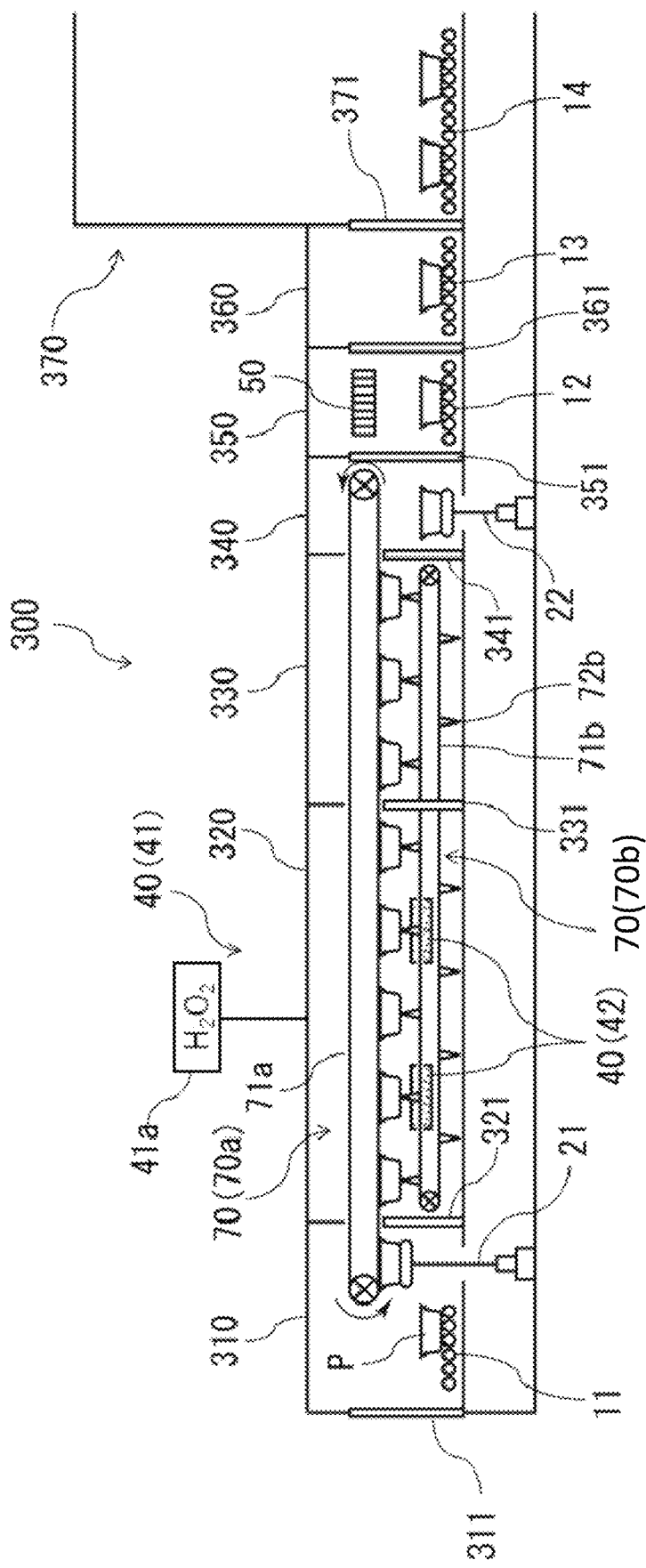
FIG. 5 is a schematic cross-sectional view illustrating a continuous decontamination and sterilization device according to a third embodiment seen in a lateral direction.

FIG. 5 is a schematic cross-sectional view illustrating a continuous decontamination and sterilization device according to a third embodiment seen in a lateral direction. In FIG. 5, a continuous decontamination and sterilization device 300 is connected to a sterile working chamber (isolator 370) for filling a pre-filled syringe therein. The continuous decontamination and sterilization device 300 is composed of a box body configured by a wall portion formed of a stainless metal plate, the inside of which is divided into a carrying pass box 310, a decontamination chamber 320, an aeration chamber 330, a prior-to-sterilization pass box 340, a sterilization chamber 350, and an after-sterilization pass box 360 by each wall portion.

A front wall portion of the carrying pass box 310 is provided with an openable/closable shutter 311. A common wall portion between the carrying pass box 310 and the decontamination chamber 320 is provided with an openable/closable shutter 321. A common wall portion between the decontamination chamber 320 and the aeration chamber 330 is provided with an openable/closable shutter 331. A common wall portion between the aeration chamber 330 and the prior-to-sterilization pass box 340 is provided with an openable/closable shutter 341. A common wall portion between the prior-to-sterilization pass box 340 and the sterilization chamber 350 is provided with an openable/closable shutter 351. A common wall portion between the sterilization chamber 350 and the after-sterilization pass box 360 is provided with an openable/closable shutter 361. A common wall portion between the after-sterilization pass box 360 and an isolator 370 connected thereto is provided with an openable/closable shutter 371.

Thus, in the continuous decontamination and sterilization device 300 according to the third embodiment, the decontamination chamber 320 for decontaminating bottom and lateral external surface portions (an external surface portion of a tab P1) of a package P is disposed on the front side.

Next, the aeration chamber 330 for removing the decontamination agent which is residual at the external surface portion of the decontaminated tab P1 is disposed. Next, the sterilization chamber 350 for sterilizing an upper surface seal portion P2 of the decontaminated and aerated package P is disposed.

Each of the chambers in the continuous decontamination and sterilization device 300 and the isolator 370 are maintained in a sterile state, each blocked from the external environment. Particularly, to prevent ingress of bacteria into the isolator 370 for filling a pre-filled syringe, the internal air pressure in each of the chambers is set to be higher than in the external environment by the air supplied from an air supply device (not shown). In addition, the air pressure of the isolator 370 is the highest, which is subsequently reduced through each of the other chambers toward the carrying pass box 310 to maintain the sterile environment.

A roller conveyor 11 and a package lift 21 are provided on the floor of the carrying pass box 310. Also, a ceiling portion from a rear portion of the carrying pass box 310 through the decontamination chamber 320, the aeration chamber 330 to the prior-to-sterilization pass box 340 is provided with a conveyance device 70 (upper conveyor 70a and lower conveyor 70b; details are later described) for sealing the upper surface seal portion P2 of the package P and conveying the same in the direction of the sterilization chamber 350. The roller conveyor 11 conveys the package P carried by opening the shutter 311 in the direction of the decontamination chamber 320. The package lift 21 receives the package P from the roller conveyor 11 at the rear portion of the carrying pass box 310 and transfers the same to the conveyance device 70 at the ceiling portion.

The conveyance device 70 seals the upper surface seal portion P2 of the received package P by the upper conveyor 70a and conveys the same to the prior-to-sterilization pass box 340 through the inside of the decontamination chamber 320 and the aeration chamber 330, with the bottom and lateral external surface portions of the package P pressed upward by the lower conveyor 70b. During this operation, the bottom and lateral external surface portions of the package P are decontaminated with a decontamination agent in the decontamination chamber 320 to remove the residual decontamination agent in the aeration chamber 330. As the package P is transferred by the conveyance device 70, the shutters 321, 331, 341 for each of the chambers are opened and closed.

The prior-to-sterilization pass box 340 is provided with a terminal portion of the conveyance device 70 and a package lift 22. The package lift 22 receives the package P from the conveyance device 70 and transfers the same to the roller conveyor 12 in the sterilization chamber 350 by opening the shutter 351. In the sterilization chamber 350, the upper surface seal portion P2 of the package P is sterilized with electron beams. The sterilized package P is transferred from the roller conveyor 12 in the sterilization chamber 350 to the roller conveyor 13 in the after-sterilization pass box 360 by opening the shutter 361. Subsequently, the package P is transferred from the roller conveyor 13 to the roller conveyor 14 in the isolator 370 by opening the shutter 371. Thus, the package P is carried in the isolator 370 as it has been decontaminated and sterilized.

Next, the conveyance device 70 will be described. The conveyance device 70 is configured by the upper conveyor 70a and the lower conveyor 70b. The upper conveyor 70a has a similar mechanism as the vacuum conveyor 30 in the above first embodiment (see FIG. 3) as a belt conveyor-type upper conveyance device by rotation of a ring-shaped wide belt which serves as a sealing member for sealing the upper surface seal portion P2 of the package P. The upper conveyor 70a is disposed integrally at the ceiling portion of the chambers from the rear portion of the carrying pass box 310 through the decontamination chamber 320, the aeration chamber 330 to the prior-to-sterilization pass box 340.

In this third embodiment, in place of a plurality of adsorption surfaces 32 (see FIG. 3) provided on a belt body 31 of the vacuum conveyor 30 in the above first embodiment, a plurality of seal surfaces is disposed on the surface of the belt body 71a of the upper conveyor 70a. The shape and size of these seal surfaces correspond to the shape and size of the upper surface seal portion P2 of the package P. Each of these seal surfaces covers the upper surface seal portion P2 of the package P to seal it from the decontamination environment inside the decontamination chamber 320. In addition, any configuration of a pad material of each seal surface may be provided, but a decontamination agent decomposition catalyst may be supported. In order to transfer the package P from the package lift 11 in the carrying pass box 310 to the upper conveyor 70a, a position adjusting mechanism (not shown) is disposed to conform the upper surface seal portion P2 of the package P to the seal surface.

Meanwhile, the lower conveyor 70b is a belt conveyor-type lower conveyance device operated with the upper conveyor 70a which serves as a pressing member for pressing upward the bottom external surface portion of the package P (a bottom external surface portion of tab P1) in the direction of the upper conveyor 70a located above. The lower conveyor 70b is integrally provided on the floor of each of the chambers from the decontamination chamber 320 to the aeration chamber 330. The belt body 71b of the lower conveyor 70b is provided on the surface with a plurality of support materials 72b. These support materials 72b form one needle-shaped column disposed vertically from a belt surface of the belt body 71b.

In such a configuration, the conveyance device 70 conveys the package P such that each seal surface 72a of the upper conveyor 70a and each support material 72b of the lower conveyor 70b individually correspond to each other and operated with each other, with the package P sandwiched vertically. Accordingly, in decontamination and aeration operations, since the upper surface seal portion P2 of the package P is entirely sealed with the seal surface 72a of the upper conveyor 70a, no decontamination agent is allowed to enter the upper surface seal portion P2 to the inside of the package P. Also, pressing the bottom external surface portion of the package P upward at one portion by point contact by the support material 72b never inhibits decontamination of the bottom external surface portion. In this third embodiment, each operation of decontamination, aeration and sterilization is performed similarly as in the above first embodiment, and such a description is omitted herein.

Thus, successfully provided in this third embodiment is a continuous decontamination and sterilization device having high decontamination and sterilization effects and high productivity and capable of maintaining high levels of reliability and safety of the decontamination and sterilization effects in a simple structure when external surfaces of a package are decontaminated and sterilized as the package is conveyed to an isolator.

Fourth Embodiment

Figure 6:
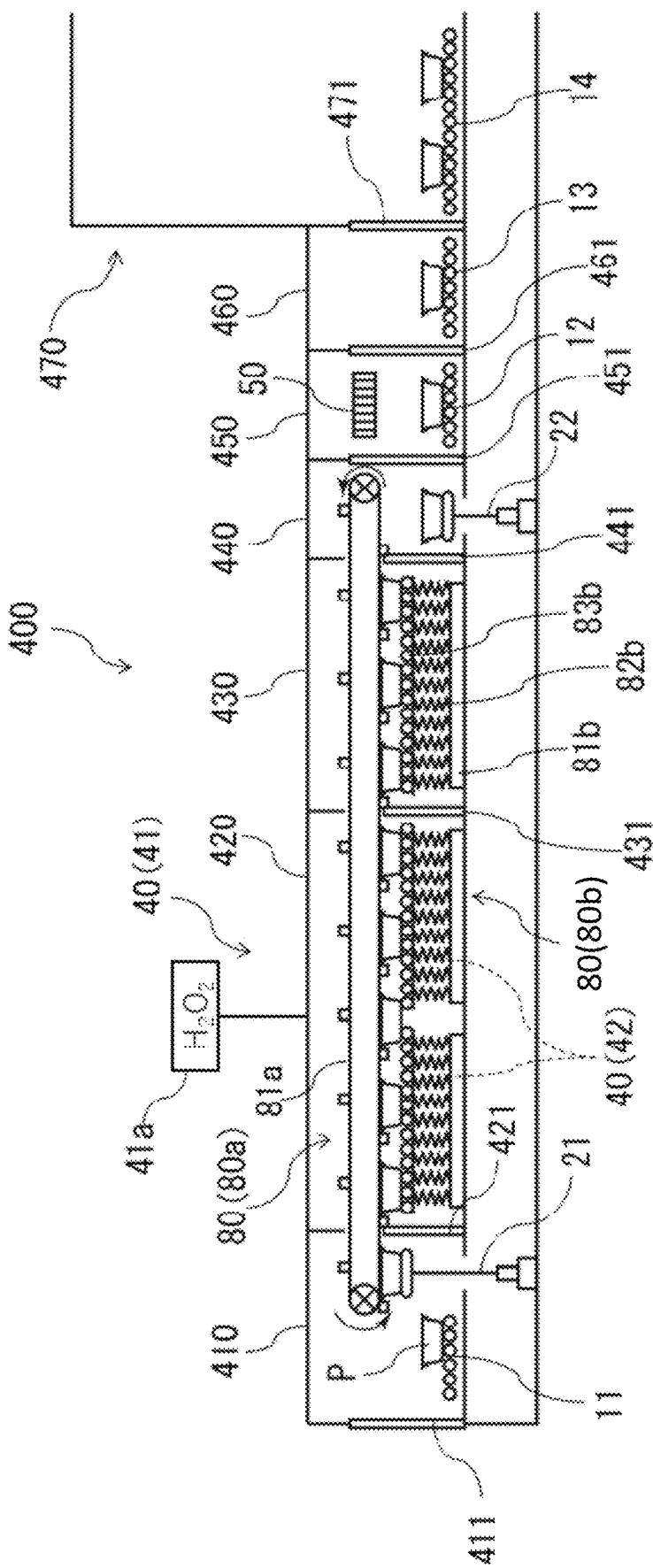
FIG. 6 is a schematic cross-sectional view illustrating a continuous decontamination and sterilization device according to a fourth embodiment seen in a lateral direction.

FIG. 6 is a schematic cross-sectional view illustrating a continuous decontamination and sterilization device according to a fourth embodiment seen in a lateral direction. In FIG. 6, a continuous decontamination and sterilization device 400 is connected to a sterile working chamber (isolator 470) for filling a pre-filled syringe therein. The continuous decontamination and sterilization device 400 is composed of a box body configured by a wall portion formed of a stainless metal plate, the inside of which is divided into a carrying pass box 410, a decontamination chamber 420, an aeration chamber 430, a prior-to-sterilization pass box 440, a sterilization chamber 450, and an after-sterilization pass box 460 by each wall portion.

A front wall portion of the carrying pass box 410 is provided with an openable/closable shutter 411. A common wall portion between the carrying pass box 410 and the decontamination chamber 420 is provided with an openable/closable shutter 421. A common wall portion between the decontamination chamber 420 and the aeration chamber 430 is provided with an openable/closable shutter 431. A common wall portion between the aeration chamber 430 and the prior-to-sterilization pass box 440 is provided with an openable/closable shutter 441. A common wall portion between the prior-to-sterilization pass box 440 and the sterilization chamber 450 is provided with an openable/closable shutter 451. A common wall portion between the sterilization chamber 450 and the after-sterilization pass box 460 is provided with an openable/closable shutter 461. A common wall portion between the after-sterilization pass box 460 and an isolator 470 connected thereto is provided with an openable/closable shutter 471.

Thus, in the continuous decontamination and sterilization device 400 according to the fourth embodiment, the decontamination chamber 420 for decontaminating bottom and lateral external surface portions (an external surface portion of a tab P1) of a package P is disposed on the front side. Next, the aeration chamber 430 for removing the decontamination agent which is residual at the external surface portion of the decontaminated tab P1 is disposed. Next, the sterilization chamber 450 for sterilizing an upper surface seal portion P2 of the decontaminated and aerated package P is disposed.

Each of the chambers in the continuous decontamination and sterilization device 400 and the isolator 470 are maintained in a sterile state, each blocked from the external environment. Particularly, to prevent ingress of bacteria into the isolator 470 for filling a pre-filled syringe, the internal air pressure in each of the chambers is set to be higher than in the external environment by the air supplied from an air supply device (not shown). In addition, the air pressure of the isolator 470 is the highest, which is subsequently reduced through each of the other chambers toward the carrying pass box 410 to maintain the sterile environment.

A roller conveyor 11 and a package lift 21 are provided on the floor of the carrying pass box 410. Also, a ceiling portion from a rear portion of the carrying pass box 410 through the decontamination chamber 420, the aeration chamber 430 to the prior-to-sterilization pass box 440 is provided with a conveyance device 80 (upper conveyor 80a and lower conveyor 80b; details are later described) for sealing the upper surface seal portion P2 of the package P and conveying the same in the direction of the sterilization chamber 450. The roller conveyor 11 conveys the package P carried by opening the shutter 411 in the direction of the decontamination chamber 420. The package lift 21 receives the package P from the roller conveyor 11 at the rear portion of the carrying pass box 410 and transfers the same to the conveyance device 80 at the ceiling portion.

The conveyance device 80 seals the upper surface seal portion P2 of the received package P by the upper conveyor 80a and conveys the same to the prior-to-sterilization pass box 440 through the inside of the decontamination chamber 420 and the aeration chamber 430, with the bottom and lateral external surface portions of the package P pressed upward by the lower conveyor 80b. During this operation, the bottom and lateral external surface portions of the package P are decontaminated with a decontamination agent in the decontamination chamber 420 to remove the residual decontamination agent in the aeration chamber 430. As the package P is transferred by the conveyance device 80, the shutters 421, 431, 441 for each of the chambers are opened and closed.

The prior-to-sterilization pass box 440 is provided with a terminal portion of the conveyance device 80 and a package lift 22. The package lift 22 receives the package P from the conveyance device 80 and transfers the same to the roller conveyor 12 in the sterilization chamber 450 by opening the shutter 451. In the sterilization chamber 450, the upper surface seal portion P2 of the package P is sterilized with electron beams. The sterilized package P is transferred from the roller conveyor 12 in the sterilization chamber 450 to the roller conveyor 13 in the after-sterilization pass box 460 by opening the shutter 461. Subsequently, the package P is transferred from the roller conveyor 13 to the roller conveyor 14 in the isolator 470 by opening the shutter 471. Thus, the package P is carried in the isolator 470 as it has been decontaminated and sterilized.

Subsequently, the conveyance device 80 will be described. The conveyance device 80 is configured by the upper conveyor 80a and the lower conveyor 80b. The upper conveyor 80a has a similar mechanism as the upper conveyor 70a in the above third embodiment as a belt conveyor-type upper conveyance device by rotation of a ring-shaped wide belt which serves as a sealing member for sealing the upper surface seal portion P2 of the package P. The upper conveyor 80a is disposed integrally at the ceiling portion of the chambers from the rear portion of the carrying pass box 410 through the decontamination chamber 420, the aeration chamber 430 to the prior-to-sterilization pass box 440.

The upper conveyor 80a is provided with a plurality of seal surfaces on the surface of the belt body 81a as in the above third embodiment. The shape and size of these seal surfaces correspond to the shape and size of the upper surface seal portion P2 of the package P. Each of these seal surfaces covers the upper surface seal portion P2 of the package P to seal it from the decontamination environment inside the decontamination chamber 420. In addition, any configuration of a pad material of each seal surface may be provided, but a decontamination agent decomposition catalyst may be supported. In order to transfer the package P from the package lift 11 in the carrying pass box 410 to the upper conveyor 80a, a position adjusting mechanism (not shown) is disposed to conform the upper surface seal portion P2 of the package P to the seal surface.

A plurality of projections 82a is disposed on the surface of the belt body 81a of the upper conveyor 80a as opposed to the above third embodiment. The projections 82a has a function of feeding in the traveling direction the package P sealed by rotation of the belt body 81a (movement in the traveling direction), with the seal surface of the belt body 81a sealing the upper surface seal portion P2 of the package P.

On the other hand, the lower conveyor 80b is not a belt conveyor-type operated with the upper conveyor 80a as opposed to the above third embodiment. In FIG. 4, the lower conveyor 80b is composed of a base 81b fixed on the floor of each of the chambers from the decontamination chamber 420 to the aeration chamber 430, a plurality of springs 82b whose one end is fixed to an upper surface of the base 81b, and a free wheel conveyor 83b placed on the other end of the plurality of springs 81b. The lower conveyor 80b serves as a pressing member for pressing upward the bottom external surface portion of the package P (a bottom external surface portion of tab P1) in the direction of the upper conveyor 80a located above by repulsion of the plurality of springs 82b.

The lower conveyor 80b is provided on the floor of each of the chambers from the decontamination chamber 420 to the aeration chamber 430. The lower conveyor 80b is not operated with the upper conveyor 80a, and when the package P is transferred in the traveling direction according to the motion of the projections 82a provided in the belt body 81a of the upper conveyor 80a, the bottom external surface portion of the package P rotates each roll of the free wheel conveyor 83b to move the bottom external surface portion of the package P between these rolls.

In such a configuration, the conveyance device 80 allows each seal surface 82a of the upper conveyor 80a and the free wheel conveyor 83b of the lower conveyor 80b to convey the package P, with the package P pressed vertically. Accordingly, in decontamination and aeration operations, since the upper surface seal portion P2 of the package P is entirely sealed with the seal surface of the upper conveyor 80a, no decontamination agent is allowed to enter the upper surface seal portion P2 to the inside of the package P. Also, pressing the bottom external surface portion of the package P upward by the rotating free wheel conveyor 83b never inhibits decontamination of the bottom external surface portion. In this fourth embodiment, each operation of decontamination, aeration and sterilization is performed similarly as in the above first embodiment, and such a description is omitted herein.

Thus, successfully provided in this fourth embodiment is a continuous decontamination and sterilization device having high decontamination and sterilization effects and high productivity and capable of maintaining high levels of reliability and safety of the decontamination and sterilization effects in a simple structure when external surfaces of a package are decontaminated and sterilized as the package is conveyed to an isolator.

The present invention is achieved not only by each of the above embodiments, but also by the following various alternatives.

(1) In the above first and second embodiments, the conveyance device employed is a vacuum conveyor, and conveyance is performed by adsorbing an upper surface seal portion P2 of a package P on a plurality of adsorption surfaces which conform the shape of the upper surface seal portion P2 of the package P to a belt body of the vacuum conveyor. However, the configuration is not restricted to that, and the entire surface of the belt body may be allowed to have an adsorption function.

(2) In the above third embodiment, a bottom external surface portion of the package P is pressed upward by point contact of a support material (one needle-shaped column) provided on a lower conveyor. However, the configuration is not restricted to that, and multiple columns may be allowed to press upward the bottom external surface portion of the package P.

(3) In each of the embodiments, a sterilization region is configured by a prior-to-sterilization pass box, a sterilization chamber, and an after-sterilization pass box. However, the configuration is not restricted to that, and only one sterilization chamber may be allowed to configure a sterilization region in consideration of X-ray shielding properties.

(4) In each of the above embodiments, the conveyance device used is often a roller conveyor for conveying the package P by supporting the bottom external surface portion of the package P. However, the configuration is not restricted to that, and a supporting conveyance device other than a roller conveyor and a sandwiching conveyance device for conveying the package P with a lateral external surface portion of the package P sandwiched may be employed.

(5) In each of the above embodiments, the way the package is transferred between chambers by a roller conveyor or a package lift is not particularly restricted. For example, an extruder such as a pusher or other transferring means may be employed.

(6) In each of the above embodiments, the mist supply unit used is a two-fluid spray nozzle. However, the configuration is not restricted to that, and an ultrasonic humidifier (nebulizer) or a single-fluid spray nozzle may be used.

(7) In each of the above embodiments, the vibrating boards of a mist circulation dispersion unit used are a plurality of ultrasonic speakers placed in a speaker base. However, the configuration is not restricted to that, and any type of vibrating board may be used so long as it includes a Langevin type transducer fixed to a stainless steel having a constant area or board surfaces for ultrasonic vibration.

(8) In each of the above embodiments, the decontamination agent used is a hydrogen peroxide solution ($H_2O_2$ solution). However, the configuration is not restricted to that, and it may be any type of decontamination agent so long as it is liquid.

REFERENCE SIGNS LIST 100 to 400 . . . Continuous decontamination and sterilization device, 110 to 410 . . . Carrying pass box,
120 to 420 . . . Decontamination chamber, 130 to 430 . . . Aeration chamber,
140, 440 . . . Prior-to-sterilization pass box, 150 to 450 . . . Sterilization chamber,
160, 460 . . . Pass box after sterilization, 170 to 470 . . . Isolator,
111 to 411, 121 to 421, 131 to 431, 141 to 441, 151 to 451, 161 to 461, 171 to 471 . . . Shutter,
11 to 15 . . . Roller conveyor, 21, 22 . . . Package lift,
30, 60, 70, 80 . . . Conveyance device, 30, 60 . . . Vacuum conveyor,
70a, 80a . . . Upper conveyor, 70b, 80b . . . Lower conveyor,
31, 71a, 71b, 81a . . . Belt body,
32 . . . Adsorption surface, 33 . . . Suction port, 40 . . . Decontamination device, 41 . . . Mist supply device,
41a . . . External storage tank, 42 . . . Mist dispersion device,
50 . . . Electron accelerator,
72a . . . Seal surface, 72b . . . Support material, 82a . . . Projection,
81b . . . Base, 82b . . . spring, 83b . . . Free wheel conveyor,
P . . . Package, P1 . . . Tab, P2 . . . Upper surface seal portion.

What is claimed is:

1. A continuous decontamination and sterilization device connected to a sterile working chamber configured to decontaminate and sterilize an external surface portion of an accommodate-package with an upper surface seal portion having gas permeability and to convey said accommodate-package to the inside of said sterile working chamber, the device comprising:
- a decontamination chamber configured to decontaminate, with a decontamination agent, a bottom external surface portion and a lateral external surface portion of said accommodate-package as the accommodate-package is conveyed by a first conveyance means, with the upper surface seal portion of said accommodate-package sealed,
- an aeration chamber configured to remove a residue of said decontamination agent from an external surface portion of said accommodate-package after decontamination as the accommodate-package is conveyed by a second conveyance means, and
- a sterilization chamber configured to sterilize the upper surface seal portion of said accommodate-package by using irradiating electron beams from an electron accelerator as the accommodate-package is conveyed by a third conveyance means, with the bottom external surface portion or the lateral external surface portion of said accommodate-package supported, wherein said first conveyance means comprises a sealing means by a pressing function, the sealing means comprising:
- a sealing member located at an upper portion of said decontamination chamber and configured to seal the upper surface seal portion of said accommodate-package and
- a pressing member located at a lower portion of said decontamination chamber and configured to press said accommodate-package from a bottom surface thereof, and
- wherein the first conveyance means is configured to convey the accommodate-package being vertically sandwiched between said sealing member and said pressing member.

2. The continuous decontamination and sterilization device according to claim 1, wherein
said pressing member is configured to press upward at least one portion of the bottom surface of said accommodate-package by point contact.

3. The continuous decontamination and sterilization device according to claim 2, wherein
said sealing member is configured to seal the upper surface seal portion of said accommodate-package by supporting a decontamination agent decomposition catalyst.

4. The continuous decontamination and sterilization device according to claim 1, wherein said decontamination chamber comprises (i) a mist supply means configured to supply to the inside of said decontamination chamber a mist for decontamination that has been converted from said decontamination agent and (ii) a mist dispersion means including an ultrasonic vibrating board configured to generate generating sound flows by ultrasound from board surfaces,
and wherein the device is configured to press said mist for decontamination, that is supplied to the inside of said decontamination chamber, by acoustic radiation pressure to decontaminate the bottom and lateral external surface portions of said accommodate-package conveyed by said first conveyance means.

5. The continuous decontamination and sterilization device according to claim 4, the device configured to transfer said accommodate-package, carried from the external environment, from said first conveyance means in said decontamination chamber to said third conveyance means in said sterilization chamber and to transfer said accommodate-package from said third conveyance means to said second conveyance means in said aeration chamber to be aerated after decontamination and sterilization.

6. The continuous decontamination and sterilization device according to claim 4, wherein
the device is configured to transfer said accommodate-package from said first conveyance means in said decontamination chamber to said second conveyance means in said aeration chamber and to transfer said accommodate-package from said second conveyance means to said third conveyance means in said sterilization chamber to be sterilized after decontamination and aeration.

* * * * *